United States Patent [19]
Task

[11] Patent Number: 5,187,541
[45] Date of Patent: Feb. 16, 1993

[54] SINGLE BEAM ANGULAR DEVIATION MEASUREMENT SYSTEM AND METHOD

[75] Inventor: Harry L. Task, Dayton, Ohio

[73] Assignee: The United States of America as represented by the Secretary of the Air Force, Washington, D.C.

[21] Appl. No.: 726,066

[22] Filed: Jul. 5, 1991

[51] Int. Cl.⁵ .......................................... G01N 21/00
[52] U.S. Cl. .................................................... 356/239
[58] Field of Search ............... 356/128, 138, 239, 127, 356/237, 129

[56] References Cited

U.S. PATENT DOCUMENTS

| | | | |
|---|---|---|---|
| 3,688,235 | 8/1972 | Migeotte | 356/239 |
| 3,693,015 | 9/1972 | Funk, Jr. | 356/129 |
| 4,249,823 | 2/1981 | Task | 356/128 |
| 4,377,341 | 3/1983 | Task et al. | 356/239 |
| 4,398,822 | 8/1983 | Task | 356/239 |

Primary Examiner—F. L. Evans
Assistant Examiner—K. P. Hantis
Attorney, Agent, or Firm—Bobby D. Scearce; Donald J. Singer

[57] ABSTRACT

System and method for measuring angular deviation in a transparency are described which comprise the steps of directing a large diameter collimated beam of light along an optical axis through a transparency, focusing a portion of the collimated beam, determining the position of the focus of the beam portion relative to the axis, repeating the above steps without the transparency, measuring any difference in position of the focus with and without the transparency, and calculating the vertical and horizontal components of angular deviation in the transparency according to relationships disclosed.

4 Claims, 2 Drawing Sheets

SINGLE BEAM ANGULAR DEVIATION MEASUREMENT SYSTEM AND METHOD

RIGHTS OF THE GOVERNMENT

The invention described herein may be manufactured and used by or for the Government of the United States for all governmental purposes without the payment of any royalty.

BACKGROUND OF THE INVENTION

The present invention relates generally to systems and methods for measuring angular deviation in a transparency, and more particularly to system and method for accurately measuring angular deviation in a transparency utilizing a single collimated light beam.

Existing systems and methods for measuring angular deviation in transparencies, and more particularly in windscreens for aircraft may be fairly exemplified by U.S. Pat. No. 4,249,823 to Task, U.S. Pat. No. 4,377,341 to Task et al, U.S. Pat. No. 4,398,822 to Task, and co-pending application Ser. No. 07/374,121 (filed Jun. 23, 1989) by Task, the teachings and background material Presented or referenced therein being incorporated herein by reference. In these references, the intersection of a line image (either a cross-hair or "L" target pattern) is utilized with a linear detector such as a one dimensional charge coupled device array to measure angular deviation. As a consequence, a small but measurable offset exists between the portion of windscreen intended for examination and the portion actually measured.

The invention solves or substantially reduces in critical importance shortcomings in the prior art as just described by Providing system and method for measuring angular deviation of a transparency unaffected by errors resulting from lateral displacement of measurement position. The invention includes a large diameter collimated light source and an angle sensing receiver system with a small diameter aperture to measure the angular deviation caused by a transparency placed in the optical Path between the collimated light source and the receiver system.

It is a principal object of the invention to provide system and method for measuring angular deviation in a transparency.

It is a further object of the invention to provide an angular deviation measurement system and method utilizing a single collimated light beam.

It is yet another object of the invention to provide system and method for accurately measuring angular deviation in a transparency wherein correction for offsets in the measurement location are not required.

These and other objects of the invention will become apparent as a detailed description of representative embodiments proceeds.

SUMMARY OF THE INVENTION

In accordance with the foregoing principles and objects of the invention, system and method for measuring angular deviation in a transparency are described which comprise steps of directing a large diameter collimated beam of light along an optical axis through a transparency, focusing a portion of the collimated beam, determining the position of the focus of the beam portion relative to the axis, repeating the above steps without the transparency, measuring any difference in position of the focus with and without the transparency, and calculating the vertical and horizontal components of angular deviation in the transparency according to relationships disclosed.

DESCRIPTION OF THE DRAWINGS

The invention will be more clearly understood from the following detailed description of representative embodiments thereof read in conjunction with the accompanying drawings wherein.

DETAILED DESCRIPTION

Figure 1:
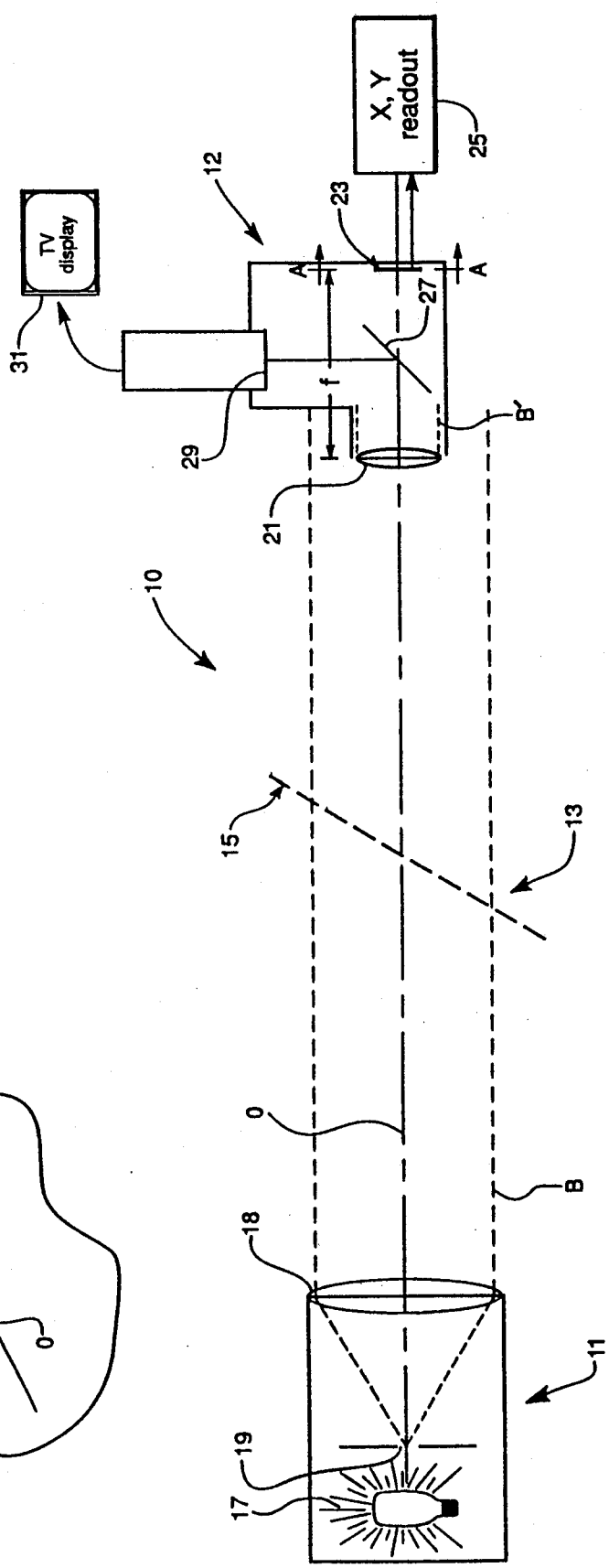
FIG. 1 is a schematic of an angular deviation measurement system according to the invention and useful in the practice of the method thereof.

Referring now to the drawings, FIG. 1 is a schematic of an angular deviation measurement system 10 of the invention. System 10 comprises two basic parts, a light source and collimating optics portion 11 and an angle sensing and receiver portion 12. Sample region 13 is defined between system portions 11,12 into which transparency 15 is inserted for examination in the practice of the invention. System portion 11 includes light source 17 for projecting test beam B along optical axis O through transparency 15. In the practice of the invention it is highly desirable that beam B be a large diameter (e.g., 2-3 inches or larger depending on a particular application) collimated, parallel beam of light. Collimating lens 18 of sufficiently large diameter is therefore disposed along axis O as shown in order to produce a desirably large beam B. Source 17 may be a laser, incandescent or other light source. For an incandescent or other incoherent source, aperture 19 (e.g., about 1/16 inch) may be needed in conjunction with large diameter collimating lens 18 to produce a sufficiently large diameter beam B.

Figure 2:
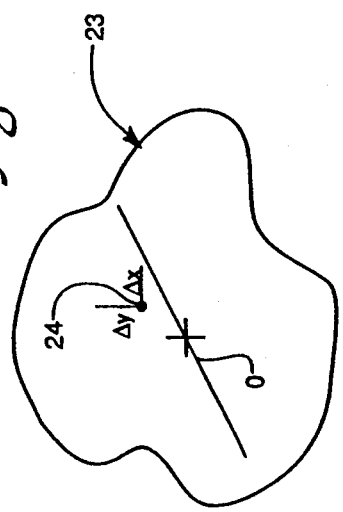
FIG. 2 is a view of the FIG. 1 system taken along line A—A showing the focus of the test beam portion on the detector.

System portion 12 includes receiver optics and detector means for measuring any displacement of a selected portion of beam B from axis O. A small diameter (about κ inch) receiver lens 21 of preselected focal length f is disposed along axis O for receiving portion B' of beam B transmitted through sample region 13. Lens 21 is of small diameter compared to the diametric size of beam B in order to define a specific portion of transparency 15 illuminated by beam B for measurement of angular deviation. Two dimensional spot detector 23 is disposed at a focal plane of lens 21 a distance f behind lens 21 and is configured to sense the position about axis O of a spot of light represented by the focus 24 of beam portion B' transmitted by lens 21. The position of focus 24 as sensed by detector 23 may be displayed on x-y readout 25, as represented by the view shown in FIG. 2. Optional beamsplitter 27 may be disposed along axis O substantially as shown in order to focus beam portion B' onto a charged couple device (CCD) array 29 disposed at a focal plane of lens 21 to alternatively detect the position of focus 24 about axis O and to display the position on television display 31. It is noted that other detection means may be used, such as a video camera with centroid tracker, calibrated electronic cross hair or other device for sensing positions of focus 24. The television display may also provide means of visually observing and confirming movement of focus 24 as beam B is swept across transparency 15 in the practice of the method of the invention described below. The horizontal and vertical movements can be fed directly to a computer for calculating the horizontal and vertical components of the observed angular deviation.

In practicing the invention, beam B is directed along axis O so that a selected portion B' is intercepted by lens 21. The x,y components of the position of focus 24 of beam portion B' (FIG. 2) are measured with no transparency in sample region 13 to provide a reference position relative to which further measurements are made. Transparency 15 is placed within sample region 13 such that beam B from source 17 is directed against the side 15a on which light would normally impinge in the operational mode, which for an aircraft transparency is the outer surface thereof. The arrangement of lenses defined by lenses 18,21 eliminates lateral displacement effects from the measurement (see Task, U.S. Pat. No. 4,398,822). The resultant effect is that any angular deviation extant in the transparency is measured with respect to a target or point of light that is (optically) an infinite distance away. With transparency 15 within sample region 13, focus 24 will be displaced from the reference position only if angular deviation is present in transparency 15 in the selected area subtended by beam B'. The vertical angular displacement $\phi$ and the horizontal angular displacement $\theta$ are related to the change in the direction of the collimated light beam caused by angular deviation within transparency 15 as follows:

$$\tan\phi \times \Delta y/f$$

$$\tan\theta \times \Delta x/f$$

where $\Delta y$ and $\Delta x$ are measured from the reference position of focus 24, f is the focal length of lens 21, and $\phi$ and $\theta$ are the vertical and horizontal angular deviations within transparency 15.

Figure 3:
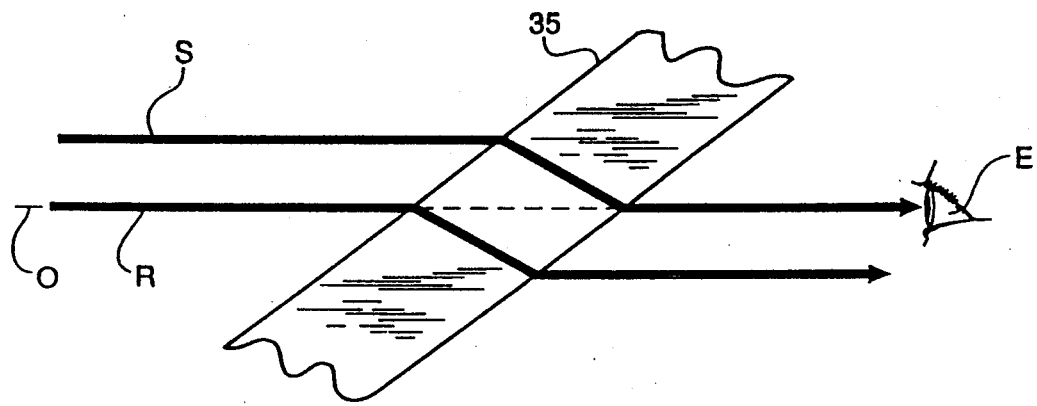
FIG. 3 shows two beams of light refracted by a transparency having no angular deviation to illustrate the physical optics principles governing the invention.
Figure 4:
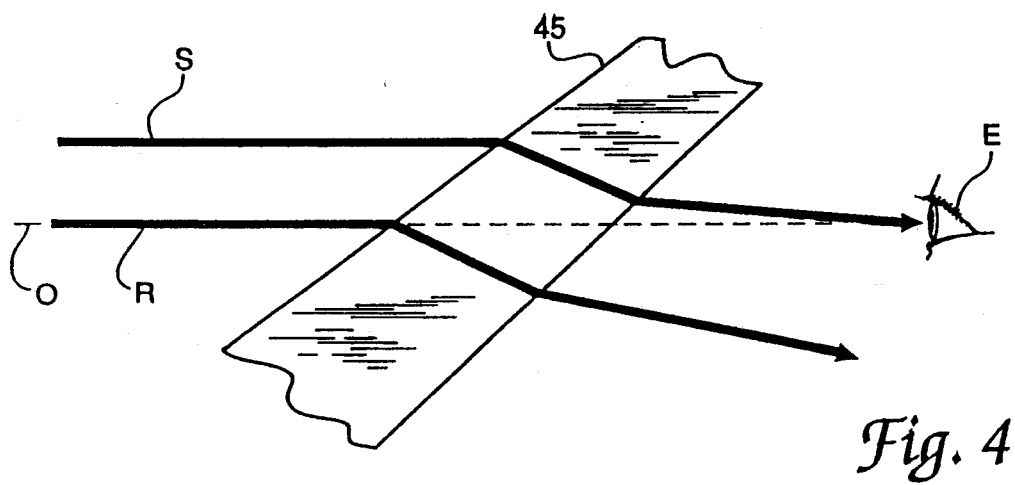
FIG. 4 shows the beams of light of FIG. 3 refracted by a transparency having a degree of angular deviation to further illustrate the optics principles governing the invention.

In order to appreciate advantages of the invention over existing angular deviation measurement methods, consider first that light from a real object at optical infinity comprises a parallel bundle of rays reaching the transparency of which a small sub-bundle of rays actually reaches an observer viewing the object through the transparency. Accurate measurement of angular deviation in the transparency requires two conditions to be met in defining the area of the transparency that should be measured for each field angle; 1) the angular direction of rays coming from the object, and 2) the ray must strike the aperture of the eye of the observer. Existing angular deviation measurement systems do not fully satisfy these two conditions. Referring now to FIG. 3, two parallel beam: R and S are shown passing through transparency 35 having no angular deviation. In FIG. 4, beams R and S are shown passing through a transparency 45 with some degree of angular deviation. If beam R is considered to originate at a target disposed distant along axis O, it is seen that by reason of the refraction of the beams by transparency 35 and of the refraction and angular deviation of transparency 45, beam R misses observer E (or a detector disposed at location E). Similarly, a beam S which is detected at E has NOT originated at the target by reason of the refraction of transparency 35 and the refraction and angular deviation character in transparency 45. In the examples of FIGS. 3,4, both conditions mentioned above are not met since light from the distant target is detected only if the interposed transparency is perfectly flat and parallel and has no angular deviation. Shifting the beam S position to coincide with axis O along which light from the target travels, and at the same time shifting the position of E to detect the refracted beam in order to meet the two conditions is not practical because the degree of shift required is dependent on the amount of angular deviation present in the transparency which is the quantity sought to be measured.

Figure 5:
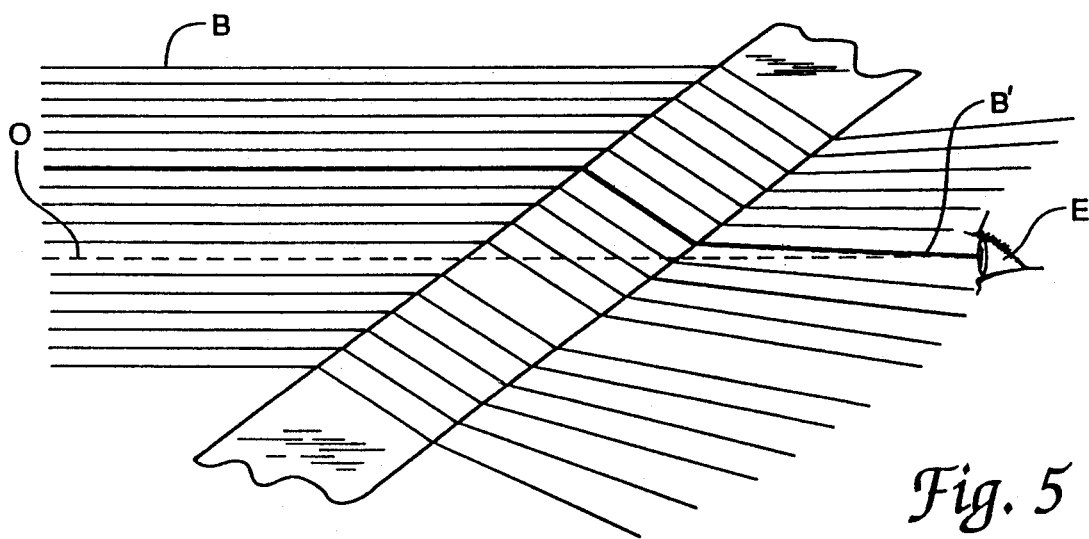
FIG. 5 illustrates a large diameter beam of collimated light utilized in the invention for selecting a portion of the transparency for measurement of angular deviation.

With reference now to FIG. 5, depicted schematically therein are the large number of light rays comprising the large diameter beam B transmitted by the collimating lens (18 in FIG. 1) parallel to axis O in accordance with the invention, which satisfies the first condition. The small diameter receiver lens (21 in FIG. 1) which collects a portion of the rays comprising beam B satisfies the second condition. Applying the procedures described above in relation to FIGS. 1 and 2 then provide a correct measurement for angular deviation in the transparency, but the exact region of the transparency that is involved in the measurement for any field angle is not known; only the field angle (direction to the target) and the eye position are known, which is what is desired.

The invention therefore provides system and method for rapidly and accurately measuring angular deviation in a transparency. The method provides internally consistent measurements without correction for offsets (refraction) in measurement location and without repeated calibration of the system. It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

I claim:
1. A system for measuring angular deviation in a transparency, comprising:
   (a) a source of light;
   (b) optical means for forming a large diameter collimated beam of light from said source and for transmitting said collimated beam along an optical axis;
   (c) a focusing lens disposed along said axis, said focusing lens being of diameter smaller than the diameter of said collimated beam for receiving a portion of said large diameter collimated beam and form forming a focus of said portion along said axis onto a focal plane of said focusing lens;
   (d) a sample region defined along said optical axis between said optical means and said focusing lens for interposing a transparency through which said large diameter collimated beam of light is transmitted in the measurement of angular deviation in said transparency; and
   (e) a detector for detecting the position of said focus on said focal plane.

2. The system of claim 1 wherein said source of light is selected from the group consisting of a laser source and an incandescent source.

3. A method for measuring angular deviation in a transparency, comprising the steps of:
   (a) directing a large diameter collimated beam of light along an optical axis through a transparency;
   (b) forming a first focus of a portion of said collimated beam, corresponding to a selected area of said transparency, onto a focal plane along said axis;
   (c) determining the position of said first focus on said focal plane;
   (d) performing the foregoing step a with said transparency removed from said collimated beam of light;
   (e) forming a second focus of said portion of said collimated beam onto said focal plane;
   (f) determining the position of said second focus on said focal plane;
   (g) comparing the positions on said focal plane of said first focus and said second focus; and
   (h) determining the degree of angular deviation in said transparency at said selected area thereof from any difference in position on said focal plane of said first focus and said second focus.

4. The method of claim 3 wherein the steps of forming said first focus and said second focus are performed using a focusing lens of known focal length and wherein the step of determining the degree of angular deviation in said transparency is performed by calculating vertical and horizontal components of said difference in position and determining angular deviation of said transparency according to the relationship:

$$\tan\phi \times \Delta y/f$$

$$\tan\theta \times \Delta x/f$$

where $\Delta y$ and $\Delta x$ are the respective said vertical and horizontal components of said difference, f is the said known focal length of said focusing lens, and $\phi$ and $\theta$ are the vertical and horizontal components of angular deviation within said transparency.

* * * * *